United States Patent [19]

Ferrari et al.

[11] Patent Number: 4,806,567

[45] Date of Patent: Feb. 21, 1989

[54] METHOD FOR THE TREATMENT OF ISCHEMIA AND REPERFUSION SYNDROMES

[75] Inventors: Vittorio Ferrari, Milan; Angelo Carenzi, Busto Arsizio; Davide Della Bella, Milan, all of Italy

[73] Assignee: Zambon S.p.A., Milan, Italy

[21] Appl. No.: 72,714

[22] Filed: Jul. 13, 1987

[30] Foreign Application Priority Data

Jul. 14, 1986 [IT] Italy ................. 21111 A/86

[51] Int. Cl.$^4$ ................. A61K 31/265; C07C 153/11
[52] U.S. Cl. ................. 514/513; 558/254
[58] Field of Search ................. 558/254; 514/513

[56] References Cited

U.S. PATENT DOCUMENTS 4,297,275 10/1981 Sundeen et al. ................. 558/254

OTHER PUBLICATIONS

Chem Abstracts, vol. 97, no. 19, abst. no. 97:163503h Nov. 8, 1982.

*Primary Examiner*—Mary C. Lee
*Assistant Examiner*—Robert C. Whittenbaugh
*Attorney, Agent, or Firm*—Stevens, Davis, Miller & Mosher

[57] ABSTRACT

A method for the treatment of ischemia and reperfusion syndromes, which consists in administering to a patient in need thereof a therapeutically effective amount of a compound of the formula:

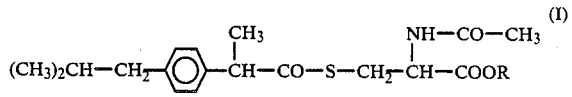

in which R is hydrogen or a $C_1-C_6$ alkyl group, or of a salt thereof, when R=H, with a pharmaeutically acceptable base.

New compounds and pharmaceutical compositions useful in the method of this invention.

1 Claim, No Drawings

METHOD FOR THE TREATMENT OF ISCHEMIA AND REPERFUSION SYNDROMES

This invention relates to a method for treating ischemia and reperfusion syndromes, which consists in administering to a patient an effective dose of a thioester of 2-(4-isobtylphenyl)-propionic acid with N-acetylcysteine or an ester thereof.

Thioesters of 2-(4-isobutylphenyl)-propionic acid with N-acetylcysteine are described in the European Pat. No. 52910.

2-(R,S)-(4-isobutylphenyl)-propionic acid is a drug endowed with anti-inflammatory, analgesic and anti-pyretic activity, known as Ibuprofen.

N-acetylcysteine is a known drug endowed with mucolytic activity.

The thioesters described in European Pat. No. 52,910 are endowed with anti-inflammatory, analgesic and anti-pyretic properties as well as with mucolytic activity and show, furthermore, an improved gastric tolerability in comparison to Ibuprofen.

Other properties were not identified in the compounds described by the above-mentioned European patent.

It is known that infarction phenomenon in the different tissues is characterized by an anoxic or ischemic condition which may be followed by a necrosis or a recovery (either spontaneous or therapeutically induced) of the oxygenation (reperfusion phase); M. Bernier et al., Circulation Research, 58, 331–340 (1986).

A specific functional alteration may take place during the reperfusion phase according to the area concerned.

For example, it is often a typical feature of the cardiac muscle during the reperfusion phase that it be afflicted by the occurence of arrhythmic phenomena, such as ectopic beat, tachycardia and fibrillation and by impairment of the contraction.

The severity of these phenomena may be high and may also cause the death of the patient through arrhythmia or cardiac shock. We have now found a method, which is an object of this invention, for the treatment of ischemia and reperfusion syndromes consisting in administering to an infarcted patient a therapeutically effective dose of a compound of the formula

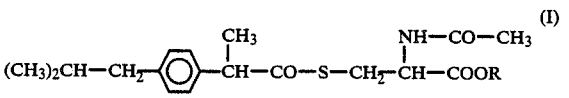

in which R is hydrogen or a $C_1$-$C_6$ alkyl group, or of a salt thereof, when R is H, with a pharmaceutically acceptable base.

The method of this invention has proved to be most effective and the compounds of formula I represent valuable means of treating ischemia and reperfusion syndromes.

There are at least two asymmetric carbon atoms (omitting any possible asymmetric carbon atoms in the substituent R when this is an alkyl) in the molecule of the compounds of formula I.

The said asymmetric carbon atoms are indicated by an asterisk and are marked by letters (a) and (b) in the following formula:

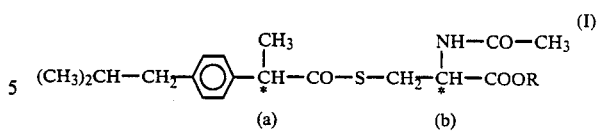

The synthesis of the compounds of formula I, according to the procedure shown further on, allows them to be obtained either as a separate diastereoisomer or as a racemic mixture.

The compounds of formula I in which R is an alkyl group are new, both as separate diastereoisomers and racemic mixtures, and they are another object of this invention.

European Pat. No. 52,910 describes the compounds of formula I, in which R is hydrogen, exclusively as a racemic mixture.

We have now found that the diasteroisomers of the compounds of formula I in which R is H and the form of the asymmetrical carbon atom (b) is (R), are particularly effective in the method for the treatment of ischemia and reperfusion syndromes, which is an object of this invention.

The following two compounds: N-acetyl-S-[(2S)-2-(4-isobutylphenyl)-propionyl]-(R)-cysteine, and N-acetyl-S-[(2R)-2-(4-isobutylphenyl)-propionyl]-(R)-cysteine, are therefore a further object of this invention, as are their salts with pharmaceutically acceptable bases.

Consequently, the new compounds of this invention are the compounds of formula I in which R is hydrogen or a $C_1$-$C_6$ alkyl group; provided, however, that when R is hydrogen the C-atoms marked by (a) and (b) have (R,R) or (S,R) configuration, and the salts thereof, when R is hydrogen, with pharmaceutically acceptable bases.

The preparation of the compounds of formula I is preferably carried out reacting 2-(4-isobutylphenyl)-propionic acid or a suitable reactive derivative thereof with N-acetylcysteine or an ester thereof, having the desired optical configuration, according to usual techniques.

Typical examples of reactive derivatives of 2-(4-isobutylphenyl)-propionic acid are the acid halides and the anhydrides. When starting from 2-(4-isobutylphenyl)-propionic acid the reaction is performed in the presence of a condensing agent such as dicyclohexyl-carbodiimide or N-hydroxy-benzotriazole.

The most preferred method comprises reacting 2-(4-isobutylphenyl)-propionic acid chloride with N-acetylcysteine or with an ester thereof in an inert solvent such as an ether, a hydrocarbon or a chlorinated hydrocarbon, in the presence of a tertiary amine such as trimethyl amine, triethyl amine or pyridine, at a temperature of between −10° and 30° C. inclusive.

N-acetylcysteine and the esters thereof may also be used in the form of a reactive derivative such as an S-trialkylsilyl derivative.

When the base is pyridine, this can act also as a solvent.

When N-acetyl-(R)-cysteine or an ester thereof is used as a starting product, the compounds of formula I are obtained in which the asymmetric carbon atom (b) has (R) configuration.

Likewise, starting from (2S)- or (2R)-2-(4-isobutylphenyl)-propionic acid chloride the compounds of formula I are obtained in which the asymmetric carbon atom (a) has (S) or (R) configuration, respectively.

Therefore, the easy availability of the starting compounds (i.e. 2-(4-isobutylphenyl)-propionic acid, N-acetyl-cysteine and the esters thereof) as a separate enantiomer allows the separate diastereoisomers of the compounds of formula I as well as their mixtures having the desired composition to be obtained.

The preparation of the salts of the compounds of formula I is carried out according to usual techniques.

Typical examples are the salts of alkali and alkaline-earth metals such as sodium, potassium, magnesium and calcium, and of organic bases such as 2-amino-ethanol, trihydroxymethylaminomethane, lysine and arginine.

The activity of the compounds of formula I in preventing the injuries caused by ischemia or reperfusion has been tested in different experimental patterns with satisfactory results. For example, the prevention of arrhythmia from reperfusion has been tested in the anesthetized rat.

In the said animal the reperfusion phase after obstruction (5 minutes) of the left coronary artery is distinguished by the occurrence of arrhythmic phenomena (ectopic beat, tachycardia and ventricular fibrillation) of varying degree, the result of which may be the death of the animal.

The protective action of the compounds of this invention has been evaluated using this model.

The parameters considered were the following:
percentual incidence of ectopic beat,
percentual incidence of ventricular tachycardia,
percentual incidence of ventricular fibrillation.

All the compounds of formula I tested showed an effective, preventive action on reperfusion arrhythmia and especially on ventricular fibrillations at doses of 2–6 mg/kg after oral administration.

The compounds of formula I proved to be well tolerated in the mouse by oral route and in the narcotized rat by intravenous perfusion, they are tolerated as Ibuprofen by oral route and better than Ibuprofen by intravenous route: more particularly, the compounds of formula I show a lack of the negative inotropic property which is typical of Ibuprofen.

Furthermore, tests for ulcerogenic activity, after repeated oral administration to the rat on an empty stomach, indicate that the compounds of formula I contrary to Ibuprofen, have poor ulcerogenic action.

Data concerning the prevention of injuries caused by ischemia and reperfusion as well as the favourable systemic and topic gastric tolerability allow the conclusion to be made that the compounds of formula I are valuable drugs in the method of treatment of this invention.

Examples of therapeutic indications are myocardial infarction, prevention of arrhythmia due to reperfusion after thrombolysis or coronary by-pass operations, acute breathing syndrome in adults and injuries caused by cerebral ischemia events.

For therapeutical purpose the compounds of formula I and the salts thereof, when R is hydrogen, with pharmaceutically acceptable bases, are preferably incorporated in a pharmaceutical dosage form suitable for oral or intravenous administration.

Depending on the desired administration route, the compositions, which are a further object of this invention, will be in the form of tablets, capsules, pills, grains and the like or of a liquid preparation ready for use or which is extemporaneously prepared by diluting a lyophilized composition.

Besides one or more compounds of formula I, the compositions according to this invention comprise a carrier or an inert diluent either solid or liquid and, optionally, other additives suitable for pharmaceutical use, and are prepared according to usual techniques.

Furthermore, for oral administration, slow-release compositions may also be used.

The effective dose of the compounds of formula I to be administered in the method for the treatment of ischemia and reperfusion syndromes according to this invention, will vary, depending on various factors such as the individual response, the age, and the general condition of the patient as well as the intended administration route.

In general, the effective dose will be from 0.2 to 4 g/day.

In order to better illustrate this invention without however limiting it, the following examples are given; H-NMR, IR spectra and elemental analysis are consistent with the indicated structure.

EXAMPLE 1

N-acetyl-S-[2-(4-isobutylphenyl)-propionyl]-cysteine (Compound No. 1)

N-acetylcysteine (16.3 g; 0.1 moles) is dissolved in anhydrous pyridine (100 ml) and de-aerated. To this solution, a solution of (R,S)-2-(4-isobutylphenyl)-propionyl chloride (25.2 g; 0.11 moles) in dichloromethane (25 ml) is added dropwise at $-5°$ C. When the addition is over the cooling bath is taken off and the stirring is continued for 2 hours.

The reaction mixture is then poured into 36% HCl (100 ml), cooled to 5° C. and extracted with ethyl ether. After evaporating the ether an oily residue is obtained (31.3 g) that is purified by chromatography on silica gel, eluting with chloroform/methanol/acetic acid (95:5:2).

The desired product (22 g) is so obtained as a colourless oil which crystallizes from isopropyl ether.
m.p.=114°–116° C.; $[\alpha]_D^{20}=0°$ (c=1%, EtOH).

EXAMPLE 2

N-acetyl-S-[(2S)-2-(4-isobutylphenyl)-propionyl]-(R)-cysteine (Compound No. 2)

To a suspension of N-acetyl-(R)-cysteine (37.95 g; 0.23 moles) in dichloromethane (350 ml) triethylamine (71.8 ml; 0.51 moles) and then trimethylchlorosilane (67.6 ml; 0.53 moles) are added drop by drop, at 0° C. in a nitrogen atmosphere. When the addition is over, the solution is kept under reflux for 1 hour, cooled to 0° C. and a solution of (2S)-2-(4-isobutylphenyl)-propionyl chloride (43.57 g; 0.19 moles) in dichloromethane (30 ml) is added dropwise.

The cooling bath is taken off and the stirring is continued for 3 hours. Dichloromethane is evaporated under vacuum at 20° C. and the residue is taken up with water and ethyl ether.

The ethereal phase is separated and dried on $Na_2SO_4$. The solvent is evaporated obtaining a white solid residue (69.5 g) which is dissolved in terbutyl ether (550 ml).

The solution is slowly diluted with pentane (1500 ml). The precipitate obtained is collected by filtration obtaining a crude product (51.5 g) which is purified by dissolution in 50% aqueous acetic acid (200 ml) and dilution with water (500 ml).

A crystalline solid precipitates which is collected by filtration and dried for some hours under vacuum.

The desired product is so obtained (49 g; 73.4% yield);

m.p. = 123°–125° C.; $[\alpha]_D^{20} = +87.9°$ C. (c=1%, EtOH)

EXAMPLE 3

N-acetyl-S-[(2R)-2-(4-isobutylphenyl)-propionyl]-(R)-cysteine (Compound No. 3)

By operating in a way similar to that described in the Example 2, and starting from N-acetyl-(R)-cysteine (39.5 g) and (2R)-2-(4-isobutyl-phenyl)-propionyl chloride (45.4 g) the desired product is obtained (18 g) as a solid melting at 102°–104° C.; $[\alpha]_D^{20} = -79.6°$ (c=1%, EtOH).

EXAMPLE 4

N-acetyl-S-[2-(4-isobutylphenyl)-propionyl]-(R)-cysteine methylester (Compound No. 4)

To a solution of N-acetyl-(R)-cysteine methyl ester (2 g; 0.011 moles) in dichloromethane (30 ml), (R,S)-2-(4-isobutylphenyl)-propionyl chloride (2.5 g; 0.012 moles) and then triethylamine (2.1 g; 0.022 moles) are added dropwise while keeping the mixture at 0° C. and under nitrogen.

When the addition is over, the cooling bath is taken off and the stirring continued for 1 hour.

The mixture is made acid by adding 1N hydrochloric acid and the organic phase is separated, washed with water and anhydrified on Na₂SO₄. After evaporating the solvent, an oily residue (4.4 g) is obtained which crystallizes from heptane. The desired product is so obtained (3.1 g; 92% yield) as a white crystalline solid melting at 44°–49° C.; $[\alpha]_D^{20} = -28.3°$ (c=1%, DMF).

EXAMPLE 5

By operating in a way similar to that described in the Example 4, the following compounds have been prepared:

N-acetyl-S-[2-(4-isobutylphenyl)-propionyl]-(R)-cysteine hexyl ester (Compound No. 5)

White crystalline solid (purified by cromatography on silica gel; eluent, ethyl acetate/petroleum ether 1:1). m.p. = 40°–45° C.; $[\alpha]_D^{20} = -2°$ (c=1%, DMF).

N-acetyl-S-[(2S)-2-(4-isobutylphenyl)-propionyl]-(R)-cysteine methyl ester (Compound No. 6)

White crystalline solid; m.p. = 75°–77° C. (heptane); $[\alpha]_D^{20} = +51.1°$ (c=1%, DMF).

N-acetyl-S-[(2S)-2-(4-isobutylphenyl)-propionyl]-(R)-cysteine hexyl ester (Compound No. 7)

White crystalline solid m.p. = 60°–62° C. (pentane); $[\alpha]_D^{20} = +47.2°$ (c=1%, DMF)

N-acetyl-S-[(2R)-2-(4-isobutylphenyl)-propionyl]-(R)-cysteine hexyl ester (Compound No. 8)

White crystalline solid; m.p. = 55°–57° C. (pentane); $[\alpha]_D^{20} = -99.8°$ (c=1%, DMF).

N-acetyl-S-[(2S)-2-(4-isobutylphenyl)-propionyl]-(R)-cysteine methyl ester (Compound No. 9)

White crystalline solid; m.p. = 88°–90° C. (pentane) $[\alpha]_D^{20} = -144.4°$ (c=1%, DMF).

We claim:

1. A method for the treatment of ischemia and reperfusion syndromes consisting in administering to a patient in need thereof a therapeutically effective amount of a compound of the formula:

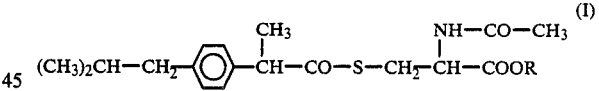

(I)

in which R is hydrogen or a $C_1$–$C_6$ alkyl group, or of a salt thereof, when R is H, with a pharmaceutically acceptable base.

* * * * *